United States Patent [19]

Zalutsky et al.

[11] Patent Number: 5,302,700
[45] Date of Patent: Apr. 12, 1994

[54] RADIOHALOGENATION CONJUGATE TECHNOLOGY

[75] Inventors: Michael R. Zalutsky, Chapel Hill; Acharan S. Narula, Durham, both of N.C.

[73] Assignee: Duke University, Durham, N.C.

[21] Appl. No.: 197,246

[22] Filed: May 23, 1988

[51] Int. Cl.$^5$ .................. C07K 15/28; C07K 17/02; A61K 49/02
[52] U.S. Cl. .................. 530/391.5; 530/345; 530/391.1; 530/391.3; 530/405; 530/409; 530/410; 424/9; 436/545; 436/547; 436/548
[58] Field of Search ............... 530/391, 345, 409, 405, 530/391.1, 391.3, 391.5, 409, 410; 424/1.1, 9; 436/545, 547, 548

[56] References Cited

U.S. PATENT DOCUMENTS

| | | | |
|---|---|---|---|
| 4,430,319 | 2/1984 | Blau et al. | 424/1.1 |
| 4,473,544 | 9/1984 | Machulla | 424/1.1 |
| 4,622,217 | 11/1986 | Wieland | 424/1.1 |
| 4,735,792 | 4/1988 | Srivastava | 424/1.1 |
| 4,826,672 | 5/1989 | Milius | 424/1.1 |
| 4,885,153 | 12/1989 | Wilbur et al. | 424/1.1 |
| 5,057,301 | 10/1991 | Wilbur et al. | 424/1.1 |

OTHER PUBLICATIONS

Abstract preparation for The Society of Nuclear Medicine 40th Annual Meeting, Toronto Convention Center Jun. 8–Jun. 11, 1993 by Garg et al.
Manuscript entitled "N-succinimidyl-4-Methyl-3-(Tri-n-Butylstannyl)benzoate:Synthesis and Potential Utility for radioiodination of Monoclonal Antibodies" by Garg et al.
Garg et al., "Labeling Proteins Using Aryl Iodide Acylation Agents: Influence of Meta vs. Para Substitution on In Vivo Stability," Nucl. Med. Biol. vol. 16, No. 7, pp. 669–673, 1989.
Wilbur, et al., "Radioiodinated Iodobenzoyl Conjugates of a Monoclonal Antibody Fab Fragment. In Vivo Comparisons with Chloramine-T-Labeled Fab," Bioconjugate Chem. 1991, 2, 111–116.
Garg et al., "N-Succinimidyl 5-(Trialkylstannyl)-3-Pyridine Carboxylates: A New Class of Reagent for Protein Radioiodination", Bioconjugate Chem., 1991, 2, 50–55.

Primary Examiner—Kay K. Kim
Attorney, Agent, or Firm—Cushman, Darby & Cushman

[57] ABSTRACT

Compounds of the formulae,

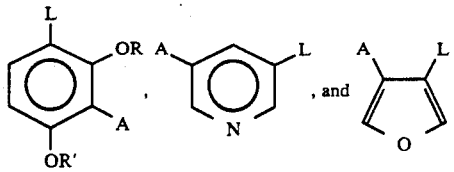

are provided where L is a linking group of the formula,

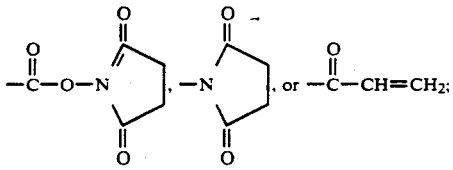

is —Sn(n—C$_4$H$_9$)$_3$ or —Sn(CH$_3$)$_3$, HgCl or —N$_2^+$; R is hydrogen, methyl, mono-, di- or oligosaccharide; and R' is methyl. The compounds are site-specifically halogenated or radiohalogenated at the A group and coupled with macromolecules such as monoclonal antibodies, peptides or other proteins.

3 Claims, 4 Drawing Sheets

RADIOHALOGENATION CONJUGATE TECHNOLOGY

FIELD OF THE INVENTION

The invention relates to methods and intermediates for radiohalogenating macromolecules, especially monoclonal antibodies, peptides and other proteins, for in vitro and in vivo diagnostic, therapeutic and investigative purposes.

BACKGROUND OF THE INVENTION

Proteins are labeled with radioactive halogen isotopes for both in vitro and in vivo study and clinical purposes. Radiohalogenated proteins are used, for example, for in vivo investigation of protein metabolism and pharmacokinetics as well as a tool for radioimmunoassays. Antibodies are labeled with halogen radioisotopes for diagnostic imaging and radiotherapy. The following table shows the applications of various halogen isotopes:

| Isotope | Half-life (hours) | Application | Type of emission | Energy (keV) |
|---|---|---|---|---|
| $^{18}F$ | 1.83 | diagnostic, PET | positron | 511 |
| $^{75}Br$ | 1.63 | diagnostic, PET | positron | 511 |
| $^{76}Br$ | 16.1 | diagnostic, PET | positron | 511 |
| $^{77}Br$ | 57.0 | diagnostic therapeutic | gamma Auger | 239 <5 |
| $^{123}I$ | 13.0 | diagnostic | gamma | 159 |
| $^{131}I$ | 193 | diagnostic therapeutic | gamma beta | 364 607 |
| $^{211}At$ | 7.2 | therapeutic | alpha | 6786 |

The development of highly specific monoclonal antibodies which can localize in cancerous tissue has increased the utility of radiohalogenated antibodies for diagnosis and therapy.

Therefore, methods have been sought to attach radiohalogens to protein molecules so that the labeled molecule remains stable to decomposition in vivo without disrupting the structure or biological function of the protein.

The strength of the aromatic carbon-halogen bond relative to that of the aliphatic carbon-halogen bond has led to the development of methods for attaching halogens to proteins through aryl-halogen bonds. Proteins may be halogenated directly or the protein may be conjugated to a separately halogenated compound.

Direct halogenation involves the substitution of halogen for a hydrogen atom on the amino acid residue of the protein. For example, a tyrosine residue may be radioiodinated ortho to the hydroxy group by the reaction of sodium iodide in the presence of an oxidizing agent at neutral pH. Other amino acid residues such as histidines, tryptophans and methionines may also be iodinated depending on reaction conditions. Common oxidizing agents for iodination of proteins are Iodogen (1,3,4,6-tetrachloro-3α,6α-diphenylglycoluril), N-bromosuccinimide and Chloromine-T (sodium N-chloro-p-toluenesulfonamide). The use of oxidizing agents for direct radioiodination of proteins, however, causes denaturation and/or chemical alteration of the binding site, reducing the biological activity of the protein. Therefore, new conjugation methods for radiohalogenation have been sought.

Conjugation involves the radiohalogenation of a small molecule which is then coupled to the protein by an acylation reaction. Bolton and Hunter first reported the now most commonly used conjugation method in their article, "The Labelling of Proteins to High Specific Radioactivities by Conjugation to a $^{125}I$-Containing Acylating Agent" 133 Biochem. J. 529-539 (1973). According to the Bolton-Hunter procedure, 3-(4-hydroxypheny 1) propionic acid N-hydroxysuccinimide ester is radioiodated ortho to the hydroxy group with Chloromine-T to obtain a compound of the formula, which reacts with the free amino groups of proteins to form an amide bond. The principal limitation of the Bolton-Hunter method is that only 30-40% of the radioactive iodine is coupled to the protein due to rapid hydrolysis of the active ester in aqueous solution. Use of the Bolton-Hunter reagent does have the advantage that more of the biological function of the protein is retained than when proteins are directly radioiodinated.

Wood et al. reported another radioiodination method in their article, "The Radioactive Labeling of Proteins with an Iodinated Amidination Reaction", 69 Analytical Biochemistry 339-349 (1975). The Wood method involves the Chloromine-T radioiodination of methyl-p-hydroxybenzimidate hydrochloride ortho to the hydroxy group to produce a compound of the formula, which reacts with protein amino groups to form an amidine linkage. Use of the Wood reagent also avoids the direct contact of deleterious oxidizing agents with the protein; however, yields of radioiodinated compound are less than 20%, even after a 24 hour reaction period.

Another major problem with the Bolton-Hunter and Woods reagents is in vivo loss of radioiodine from the protein. Unassociated radioiodine accumulates in the thyroid and stomach and appears in the urine after administration of radioiodinated antibodies. Dehalogenation is believed to occur in vivo by hydrolytic and enzymatic processes as well as those mediated by binding of the protein to a cell. The Bolton-Hunter and Woods methods involve radiohalogenation of a phenyl ring which is activated by a hydroxy group, causing substitution at the ortho position. The presence of the hydroxy group ortho to the radiohalogen, however, renders the conjugate susceptible to both hydrolytic and enzymatic in vivo dehalogenation. Therefore, radiohalogenated conjugates which do not have a hydroxy group ortho to the halogen label on the phenyl ring have been sought.

Wilbur et al. European Patent 0 203 764 discloses substitution of radiohalogen on a non-activated aromatic ring for conjugation to proteins. According to Wilbur et al., a haloaryl compound is initially converted into an aryllithium compound, which, upon transmetalation with $R_3SnCl$ ($R=n-C_4H_9$ or $CH_3$), $HgX_2$, $BX_3$ ($X=$halogen), or $BZ_3$ ($Z=$alkyl or alkoxy), gives an appropriate organometallic derivative of Sn, Hg or B. Such organometallic derivatives are then utilized for site-specific radiohalogenation. The Wilbur et al. aryl compounds also have a non-activating short-chain substituent bearing a functional group suitable for conjugation to protein under conditions that preserve the biological activity of the protein.

Applicants have reported the radioiodination of proteins using the iodinated derivative, N-succinimidyl 3-(tri-n-butylstannyl) benzoate (Activated Tin-containing Ester, hereinafter "ATE") having the formula, Zalutsky et al., "A Method for the Radiohalogenation of Proteins Resulting in Decreased Thyroid Uptake of Radioiodine", 38 *Appl. Radiat. Isot.* 1051-1055 (1987). Radioiodination of ATE achieves 80% yield and proteins are coupled with the resulting labeled compound with greater than 60% efficiency. In vivo dehalogenation of [$^{125}$I]ATE-labeled goat IgG is reduced compared with dehalogenation goat IgG labeled using the Iodogen method.

SUMMARY OF THE INVENTION

The object of the present invention is to provide methods for labeling macromolecules, especially monoclonal antibodies, peptides and other proteins, with radioactive halogen atoms in a manner which preserves biological activity and minimizes loss of the radioactive halogen nuclide from the macromolecule in vivo. A further object of the invention is to provide intermediate compounds that can be specifically radiohalogenated and that can be readily conjugated to antibodies and other proteins as well a method for synthesizing the intermediate. A still further object of the invention is to provide an aromatic compound for conjugation to macromolecules which is highly stable to in vivo dehalogenation due to the following substitution pattern: an electron withdrawing group in position 1, electron donating groups in positions 2 and 4 and position 3 being the site of radohalogenation. A still further object of the invention is to provide heterocyclic aromatic compounds with a $\pi$-electron deficient aromatic template for forming a highly stable conjugate with macromolecules.

Therefore the invention provides a compound (I) of the formula, where A is a group selected from $-SnR''_3$, $-HgCl$ and $-N_2^+$;

L is a linking group selected from the following structures,

R is hydrogen, methyl, mono-, di-, or oligosaccharide; R' is $CH_3$; and R'' is n-butyl or methyl.

The invention also provides a compound (Ia) of the formula, where L, R, R' and R'' are defined as above, and X is a radioactive halogen selected from $^{18}F$, $^{75}Br$, $^{76}Br$, $^{77}Br$, $^{123}I$, $^{125}I$, $^{131}I$, and $^{211}At$.

The invention also provides compounds (II), (IIa), (III) and (IIIa) of the formulas, where A, L, and X are defined as above.

The invention further provides a method for radiohalogenating macromolecules by coupling a compounds of formula (Ia), (IIa) and (IIIa) to a macromolecule such as an antibody or other protein.

DETAILED DESCRIPTION OF THE INVENTION

In the 1,2,3,4-tetra substituted aromatic compounds of formula (I), the A substituent provides the site for a regiospecific introduction of a stable halogen or a radiohalogen at a no carrier added level. The nature of the R substituent can determine the lipophilic or hydrophilic character of the compound (I). Any group capable of manipulating the polarity of compound (I) can be used as the R substituent. By altering the physical properties of the molecule, the mechanisms for in vivo stability and clearance of compound (I) can be controlled.

In compound (Ia), the electron-donating groups at positions ortho to the halogen strengthen the carbon-halogen bond. Further, substitution at these ortho positions helps block decomposition by preventing epoxide formation and creating steric hindrance for attack at the halogen carbon.

A representative example of the compound of formula (I) is N-succinimidyl-2,4-dimethoxy-3-(tri-n-butylstannyl)benzoate (hereinafter "SDMB"). The synthesis of this compound and a corresponding radiolabeled compound, N-succinimidyl-2-4-dimethoxy-3-[$^{125}$I]benzoate, are shown in Examples 1 and 2.

A representative example of formula (II) is N-succinimidyl-5-(tri-n-butylstannyl)-3-pyridine carboxylate (hereinafter "SPC"). The synthesis of this compound and the corresponding radio-labeled compound, N-succinimidyl-5-[$^{125}$I]iodo-3-pyridine carboxylate is shown in Examples 3 and 4. The coupling of the radiolabeled compound SPC with proteins and in vitro and in vivo evaluation of the resulting protein conjugates is shown in Examples 5–7.

The radiolabeled compounds of formulae Ia, IIa and IIIa may be conjugated to macromolecules such as monoclonal antibodies, peptides and other proteins. The radiolabeled compounds are incubated with the macromolecule, and high yields of the conjugates are obtained.

The radiolabeled compounds of formulae Ia, IIa and IIIa can readily couple covalently with monoclonal antibodies and other proteins. This is demonstrated by both in vitro and in vivo studies. The uptake of radioiodide by the thyroid and stomach in mice, for example, is considerably less for SPC protein conjugates than for proteins radiolabeled with Iodogen or ATE protein conjugates (see p. 6, supra). This result is also obtained in athymic mice bearing a human colorectal carcinoma xenograft, even though such mice have an increased rate of catabolism. Thus, the compounds and methods of the present invention show considerable advantage over prior art compounds and methods for radiohalogenating macromolecules.

The invention is further illustrated by the following non-limiting examples.

EXAMPLE 1

Synthesis of N-succinimidyl-2,4-dimethoxy-3-(tri-n-butylstannyl) benzoate (SDMB)

N-succinimidyl-2,4-dimethoxy-3-(tri-n-butylstannyl) benzoate [Formula I, L=N-hydroxysuccinimidyl ester, R=—CH$_3$, R'=—CH$_3$ and A=—Sn(n-C$_4$H$_9$)$_3$] was synthesized via lithium 2,4-dimethoxy-3-lithiobenzoate (2), which was obtained from 2,4-dimethoxy-3-bromobenzoic acid (3b) by metal-halogen exchange with n-butyl lithium:

(3a) X = I
(3b) X = Br
(2)

SDMB was obtained by the following successful sequence of reactions:

(a) Hg(OAc)$_2$—EtOH/CH$_3$COOH; NaBr—H$_2$O;
(b) Br$_2$/CHCl$_2$;
(c) Na$_2$CO$_3$/CH$_3$I; (CH$_3$)$_2$C=O;
(d) Jones Reagent;
(e) 2.2 eq. n-BuLi, THF, −100° C.; 2.5 eq. n-Bu$_3$SnCl;
(f) NHS/DCC Treatment of 2-hydroxy-4-methoxybenzaldehyde (4) with mercuric acetate in refluxing alcohol containing ≈1% acetic acid followed by treatment with aq. NaBr gave an over 85% yield a 6:1 mixture of organo-mercury compounds (5) and (6) m.p. ≈200° C., [$^1$H-NMR: (300 MHz CDCl$_3$, δ): compound (5): 3.90 (s, 3H, C4—OCH$_3$), 6.70 and 7.55 (pair of doublets, Jab=8 Hz, C5—H and C6—H), 9.80 (s, 1H, H—C=O) and 11.33 (s, 1H, Φ—OH): compound (6): 3.80 (s, 3H, C4—OCH$_3$), 6.50 (s, 1H, C3—H), 7.46 (s, 1H, C6—H), 9.70 (s, 1H, HC=O) and 11.64 (s, 1H, Φ—OH.] The ratio of two compounds from this reaction was obtained from the integration of the phenolic and aldehydic absorption assigned above.

Treatment of the above mixture of organo-mercury compounds (5 and 6) with one equivalent of bromine in CHCl$_3$ containing a small amount of acetic acid gave, after the usual work-up and purification over silica gel (elution with 30% EtOAc in hexane), an ≈56% yield of the pure 3-bromo-2-hydroxy-4-methoxybenzaldehyde (7), m.p. 115°-117° C. [$^1$H-NMR; (300 MHz, CDCl$_3$, δ): 4.0 (s, 3H, C4—OCH$_3$), 6.50 and 7.52 (pair of doublets, Jab=8Hz, C5—H and C6—H), 9.75 (1H, s, HC=O), 11.96 (1H, s Φ—OH). Mass: m/e 230, 232 C$_8$H$_7$O$_3$Br (M+, 88.8%, 86.9%).

Methylation of the phenolic OH in (7) with MeI/Na$_2$CO$_3$, proceeded readily to give 3-bromo-2,4-dimethoxybenzaldehyde (8), m.p. 80° [$^1$H-NMR: (300 MHz, CDCl$_3$, δ): 4,0 (s, 2×3H, C2 and C4-OCH$_3$), 6.82 and 7.84 (pair of doublets, Jab=8 Hz, C5-H and C6-H), 10.30 (s, 1H, HC=O. Mass: m/e 244, 246 C$_9$H$_9$O$_3$Br (M+, 63.3%, 61.5%).

Jones oxidation of (8) gave in 83% yield 2,4-dimethoxy-3-bromobenzoic acid [3b. m.p. 175°-177° C; $^1$H-NMR (300 MHz, CDCl$_3$, δ): 4.0 & 4.04 (s, 2×3H, C2 and C4-OCH$_3$), 6.83 and 8.81 (pair of doublets, Jab=8Hz, C5-H and C6-H), 10.8 (bs, 1H, COOH); Mass: m/e 260, 262 C$_9$H$_9$O$_4$Br (M+, 100%, 97.3%).

Treatment of (3b) with 2.2 eq. of n-BuLi in THF at −100° C. under argon, followed by warming to −80° C. for 30 min. generated the desired dilithio-anion (2), which was quenched with ≈2.5 eq. of tri-n-butyl tin chloride. The desired tri-n-butylstannyl-2,4-dimethoxy-3(tri-n-butylstannyl)benzoate (9) was isolated from the neutral fractions by silica gel chromatography (eluant: 10% ether in CHCl$_3$, yield ≈45% relative to 3).

Because of the labile nature of the tri-n-butyl tin ester, this product was directly converted to N-succinimidyl-2,4-dimethoxy-3-(tri-n-butylstannyl)benzoate (SDMB). The assigned structure for SDMB was in full agreement with its spectral data: $_1$H-NMR: (300 MHz, CDCl$_3$, δ); 0.90-1.48 (typical m, 27H, 3×n-C$_4$H$_9$); 2.91 (s, 4H, —CO—CH$_2$—CH$_2$—CO); 3.76 (s, 3H, OCH$_3$); 3.88 (s, 3H, OCH$_3$); 6.66 and 8.12 (pair of doublets, Jab=8 Hz, C5—H and C6-H). FAB-Mass: m/e 512 [(C$_{25}$H$_{39}$O$_6$Sn-)—(C$_4$H$_9$)] (M+—57, 40%), 455 (M+—C$_4$H$_4$NO$_3$, 66%), 285 [(455—3 ×C$_4$H$_9$) +H, 32%], 165 [(285 -Sn), 100%].

EXAMPLE 2

Iodination and Radioiodination of N-succinimidyl-2,4-dimethoxy-3-(tri-n-butylstannyl) benzoate (SDMB)

In order to characterize the radioiodinated product (14) from SDMB, and authentic sample of N-succinimidyl-2,4-dimethoxy-3-iodobenzoate (14) was first prepared by the condensation of N-hydroxysuccinimide and 2,4-dimethoxy-3-iodobenzoic acid (3a) in the presence of dicyclohexyl carbodimide:

N-Succinimidyl-2,4-dimethoxy-3-iodobenzoate (14): 2,4-Dimethoxy-3-iodobenzoic acid (2) required for the synthesis of (14) was readily prepared according to the following sequence of reactions:

(a) Hg(OAc)$_2$—EtOH, AcOH;
(b) I$_2$/CHCl$_3$
(c) CH$_3$I/K$_2$CO$_2$-acetone
(d) Jones Reagent Treatment of 2-hydroxy-4-methoxy-benzaldehyde (4) with mercuric acetate in refluxing alcohol containing ≈1% AcOH gave in over 91% yield a 6:1 mixture of organo-mercury compounds (10) and (11).

Treatment of this mixture with iodine in CHCl$_3$ afforded after purification over silica gel (elution with 30% EtOAc in hexane) in ≈60% yield the pure 3-iodo-2-hydroxy-4-methoxybenzaldehyde (12), m.p. 100.C, [$^1$H-NMR: (300 MHz, CDCl$_3$, δ): 4.0 (s, 3H,C4-OCH$_3$), 6.52 and 7.52 (pair of doublets, Jab=8 Hz, C5—H and C6—H), 9.70 (1H, s, HC=O), 12.20 (1H, s, Φ—OH)].

Methylation of the phenolic —OH group in (12) with MeI-K$_2$CO$_3$ in refluxing acetone proceed smoothly to give 2,4-dimethoxy-3-iodobenzaldehyde (13), m.p. 103.3° C. [$^1$H-NMR: (90 MHz, CDCl$_3$, δ): 3.90 (overlapping s, 2×3H, C2 and C4-OCH$_3$), 6.62 and 7.78 (pair of doublets. Jab=8Hz, C5-H and C6-H), 10.12 (s, 1H, HC=O).]

Jones oxidation of (13) gave in ≈82% yield 2,4-dimethoxy-3-iodobenzoic acid (3a), m.p. 182° C. [$^1$H-NMR: (90 MHz, CDCl$_3$, δ): 4.0 (overlapping singlets, 2×3H, C2 and C4—OCH$_3$), 6.84 and 8.22 (pair of doublets, Jab=8 Hz, C5-H and C6—H), 10.30 (broad signal, 1H, COOH).]

Treatment of this acid (3a) with N-hydroxysuccinimide in the presence of dicyclohexyl carbodiimide gave, after usual workup, the pure N-succinimidyl-2,4-dimethoxy-3-iodobenzoate (14), m.p. 163°-165° C. [$^1$H-NMR: (90 MHz, CDCl$_3$, δ): 2.90 (s, 4H, —CO—CH$_2$—CH$_2$—CO—), 3.86 and 3.94 (pair of singlets, 2×3H, C2—OCH$_3$ and C4—OCH$_3$), 6.770 and 8.10 (pair of doublets, Jab=8 Hz, C5-H and C6-H)]. Mass: m/e 405 C$_{13}$H$_{12}$O$_6$NI (M$^+$, 5.4%), 291 (M+—C$_4$H$_4$NO$_3$, 100%).

Cold iodination of N-succinimidyl-2,4-dimethoxy-3-(tri-n-butylstannyl)benzoate (SDMB): Four standard solutions were prepared as follows:

(a) 15 mg of NaI in 100 μl of 0.01N NaOH;
(b) 6 mg of acetic acid in 100 μl of CHCl$_3$;
(c) 9.0 mg TBHP (90%, containing 5% H$_2$O and 5% tert-butyl alcohol) in 100 μl of CHCl$_3$ and a few crystals of anhydrous Na$_2$SO$_4$;
(d) 5.5 mg of SDMB in 100 μl of CHCl$_3$.

In a 1 ml conical vial, 20 μl of reagent (d) was added to 10 μl each of reagent (a), (b) and (c). The mixture was stirred magnetically at room temperature for 30 min. and then the magnet was withdrawn and washed with 50 ml of CHCl₃. A TLC examination (silica gel, 50% EtOAc in hexane) showed in addition to SDMB at $R_f$ 0.37, a new spot at $R_f$ 0.18. This spot had the same $R_f$ value as that of an authentic sample of N-succinimidyl-2,4-dimethoxy-3-iodobenzoate (14) prepared as described above. The isolation of N-succinimidyl-2,4-dimethoxy-3-iodobenzoate (14) was readily accomplished by chromatography over silica gel Sep Pak cartridge. The Sep Pak cartridge was initially saturated with hexane and then the above reaction mixture to be separated was loaded over the column with the help of 200–400 μl of hexane. The column is then eluted with hexane (35–40 ml), 8% EtOAc in hexane (30–35 ml) and finally with 30% EtOAc in hexane (1 ml×3; 15 ml). The first 3 ml of the 30% EtOAc in hexane fraction was discarded and the remaining 15 ml fraction was concentrated to give pure N-succinimidyl-2,4-dimethoxy-3-iodobenzoate.

Radioiodination of SDMB: to 1.42 mCi of Na[$^{125}$I] in 20 μl of pH 7–10 NaOH in a 1 ml conical vial were added 50 μl each of reagents (b) and (c), followed by 10 μl of reagent (d), as described above. The reaction mixture was stirred at room temperature for 30 min. The magnetic bar was withdrawn and washed with 50 μl of CHCl₃. The reaction mixture was then concentrated under a slow stream of nitrogen and loaded over a Sep Pak silica gel cartridge with the help of 300–500 μl of hexane. Residual activity in the 1 ml conical vial was ≈35 μCi.

Isolation of the desired labeled N-succinimidyl-2,4-dimethoxy-3[$^{125}$I]-iodocarboxylate, was achieved by collecting the following pooled fractions:

| Fraction No. | | Solvent | Vol. | Activity |
|---|---|---|---|---|
| 1 | (i) | hexane | 10 ml | 22.80 μCi |
|   | (ii) | hexane | 10 ml | 5.70 μCi |
|   | (iii) | hexane | 10 ml | 4.10 μCi |
|   | (iv) | hexane | 10 ml | 3.50 μCi |
| 2 | (i) | 8% EtOAc in hexane | 10 ml | 76.50 μCi |
|   | (ii) | 8% EtOAc in hexane | 10 ml | 8.86 μCi |
|   | (iii) | 8% EtOAc in hexane | 10 ml | 3.80 μCi |
| 3 | (i) | 30% EtOAc in hexane | 1 × 3 ml | 4.22 μCi |
|   | (ii) | 30% EtOAc in hexane | 1 ml | 7.20 μCi |
|   | (iii) | 30% EtOAc in hexane | 5 ml | 567.00 μCi |
|   | (iv) | 30% EtOAc in hexane | 5 ml | 977.00 μCi |
|   | (v) | 30% EtOAc in hexane | 5 ml | 144.00 μCi |
|   | (vi) | 30% EtOAc in hexane | 5 ml | 11.00 μCi |

Fractions 3 (iii to v) above amounting to 91.9% of the eluted activity was shown by silica gel TLC and HPLC analysis to be pure N-succinimidyl-2,4-dimethoxy-3[$^{125}$I]-iodocarboxylate (14).

EXAMPLE 3

Synthesis of N-succinimidyl-5-tri-n-butylstannyl-3-pyridine carboxylate (SPC)

(a) 2.2 eq. n-BuLi/THF, −100° C.
(b) (n-C₄H₉)₃SnCl (2.5 eq.)
(c) NHS—DCC/THF, 3 days, RT Synthesis of compound (18) was readily accomplished in three steps starting from commercially available 5-bromo-3-pyridine carboxylic acid (15). Treatment of (15) with 2.2 eq. of n-BuLi in THF at −100° C. gave lithium 5-lithio-3-pyridine-carboxylate (16) in 30–36% yields. The reaction also gave products which are presumed to be derived by the addition of n-butyllithium across the C=N of the pyridine ring in (15).

After quenching the above reaction mixture with (n-C₄H₉)₃SnCl and purifying the neutral fractions over silica gel, two products were obtained which were readily separable by silica gel column chromatography (silica gel TLC, 2% AcOH in 30% EtOAc-hexane, $R_f$ 0.50 and 0.16).

The compound with lower $R_f$ (0.16) was shown by $^1$H-NMR to consist of product (17). The confirmation of the assigned structure was based on its conversion in ≈83% yield to N-succinimidyl-5-tri-n-butylstannyl-3-pyridine carboxylate (18). [$^1$H-NMR: (300 MHz, CDCl₃, δ): 0.90–1.50 (typical m, 27H, 3×n-C₄H₉); 2.82 (s, 4H, —CO—CH₂—CH₂—CO—), 8.40 (s, 1H, C6—H), 8.85 (s, 1H, C4-H), 9.22 (s, 1H, C2-H)]. Mass: C₂₂H₃₄O₄NSn 453 (M⁺—n-C₄H₉, 82%), 396 (M⁺—C₄H₄NO₃, 20%), 339 (M⁺—3×C₄H₉, 8%), 226 (100%).

Treatment of (18) with iodine readily gave N-succinimidyl-5-iodo-3-pyridine carboxylate, further supporting the assigned structure to (18).

EXAMPLE 4

Iodination and Radioiodination of N-succinimidyl-5-tri-n-butylstannyl-3-pyridine carboxylate (SPC)

In order to find suitable conditions for the radioiodination of SPC, the cold iodination of SPC was investigated. After considerable experimentation, it was found that the following procedure worked quite efficiently.

Iodination (cold) of SPC: Two standard solutions were prepared as follows: (a) 6 mg acetic acid in 100 µl of $CHCl_3$; (b) 5.6 mg of SPC in 100 µl of $CHCl_3$.

In a 1-ml conical vial, 50 µl of (b) was added to 8 µl of (a), followed by a crystal of $I_2$. The reaction mixture immediately acquired the violet color of iodine. Upon warming the reaction mixture for 20-25 minutes in an oil bath at 70°-80° C., a faint color indicative of free iodine still persisted. Examination by silica gel TLC (solvent system: 1% AcOH in 1:2:2 EtOAc, hexane, $CH_2Cl_2$) revealed the total consumption of the starting material (SPC) and formation of a new product at $R_f$ 0.29. This material was readily isolated by preparative layer TLC on silica gel and was shown by its spectral data ($^1$H-NMR, Mass Spectrum) to be the desired N-succinimidyl-5-iodo-3-pyridine carboxylate, m.p. 174.5° C.

Radioiodination of SPC: Three standard solutions were prepared as follows (A) 6 mg acetic acid in 100 µl of $CHCl_3$; (b) 9 mg of 90% t-butylhydroperoxide (TBHP) in 100 µl of $CHCl_3$ containing a few crystals of anhyd. $Na_2SO_4$; (c) β5.6 mg of SPC in 100 µl of $CHCl_3$.

A typical preparation is described below. In a 1-ml conical vial containing 50 µl of $CHCl_3$, was added 0.55 mCi of Na[$^{125}$I]in 10 µl of pH 7-11 NaOH, 20 µl each of reagent (a) and (b) and 10 µl of (c). The reaction vial was capped with a teflon top and screwed tightly closed. After warming in oil bath ($\approx 80°14~85°$ C.) for 20-25 minutes, the reaction mixture was allowed to come to room temperature and the product was chromatographed over a Sep Pak silica gel cartridge. The following pooled fractions were collected:

| S. No. | Solvent | Vol. | Activity |
| --- | --- | --- | --- |
| 1 | 1:1 $CH_2Cl_2$-hexane | 10 ml | — |
|  | 1:1 $CH_2Cl_2$-hexane | 10 ml | 26.8 µCi |
| 2 | $CH_2Cl_2$ | 10 ml | 25.8 µCi |
| 3 | 50% EtOAc in 1:1 $CH_2Cl_2$-hexane | | |
|  | (i) | 1 ml | 2.3 µCi |
|  | (ii) | 1 ml | 83.6 µCi |
|  | (iii) | 3.5 ml | 382.8 µCi |
|  | (iv) | 0.5 ml | 2.2 µCi |

Fraction 3(ii) above amounting to $\approx 73\%$ of the eluted activity was concentrated under vacuum and transferred with the help of $\approx 150$ µl of $CHCl_3$ into a 1 ml dram vial and evaporated to dryness.

EXAMPLE 5

Coupling of monoclonal antibody-110 (MAb-110) with N-succinimidyl-5-[$^{125}$I]-iodo-3-pyridine carboxylate MAb-110 (300 µg) in 50 µl of 100 mM borate buffer, pH $\approx 8.5$ was added to the labeled N-succinimidyl-5-[$^{125}$I]-iodo-3-pyridine carboxylate (Fraction 3(ii) above) in a 1 ml dram vial and the mixture was incubated at 4° C. for 30-35 minutes. The labeled protein was isolated over a Sephadex G-25 column. The yield of the labeled protein was 40%.

EXAMPLE 6

In vitro evaluation of N-succinimidyl-5-[$^{125}$I]iodo-3-pyridine carboxylate—monoclonal antibody conjuqate.

These studies were performed using the anti-CEA monoclonal antibody 110 as a model system. Monoclonal antibody 110 was labeled with either I-131 or I-125 via SPC as described in Example 5 and serially diluted from 2500 to 1.25 µg/50 µl in phosphate buffered saline containing 0.1% bovine serum albumin (PBS/BSA). Aliquots in triplicate of each dilution were added to 96-well microtiter plates containing either LS174T membranes (1 µg/50 µl, containing approximately 250 ng of CEA) or as a negative control, BSA (1 µg/50 µl). Plates were incubated either overnight at 4° C. or at room temperature for 4 hours. Plates were washed three times in 1% PBS/BSA and then dried. The binding data were analyzed by Scatchard analyses using the EBDA/Ligand computer program. The affinity constant of Ab 110 labeled with either I-125 or I-131 was calculated to be $(1.25\pm 0.17)\times 10^9$ $M^{-1}$.

EXAMPLE 7

In vivo evaluation of N-succinimidyl-5-[$^{125}$I]iodo-3-pyridine carboxylate protein conjuqates.

When radioiodine is released from proteins following in vivo administration, loss of label occurs (dehalogenation). Since free iodide is taken up avidly by the thyroid and, at early time points, localizes in the stomach, uptake of radioiodine by these tissues is often used as an indicator of dehalogenation in vivo.

The method of choice for comparing the pharmacokinetics of two radioiodinated products (or two samples of the same compound, each sample radioiodinated using a different method) is to administer both to the same group of animals, labeling the first with $^{125}$I and the second with $^{131}$I. By performing "paired-label" experiments, one can correct for systematic errors such as incomplete thyroid sampling (less than 10 mg in a mouse) which could make intragroup comparisons difficult.

In the first paired-label study, groups of mice were injected with both [$^{131}$I]iodide and 5-$^{125}$I]iodonicotinic acid (hereinafter INA), the labeled substrate which is attached to proteins in the SPC procedure. As shown in Table 1, the percentages of the injected dose of INA which localize in the thyroid, and at early time points, the stomach, are significantly lower than those observed with iodide. For thyroid, uptake of $^{125}$I is 23-56 times lower than $^{131}$I, suggesting that the INA template is relatively inert to dehalogenation in vivo.

Figure 1:
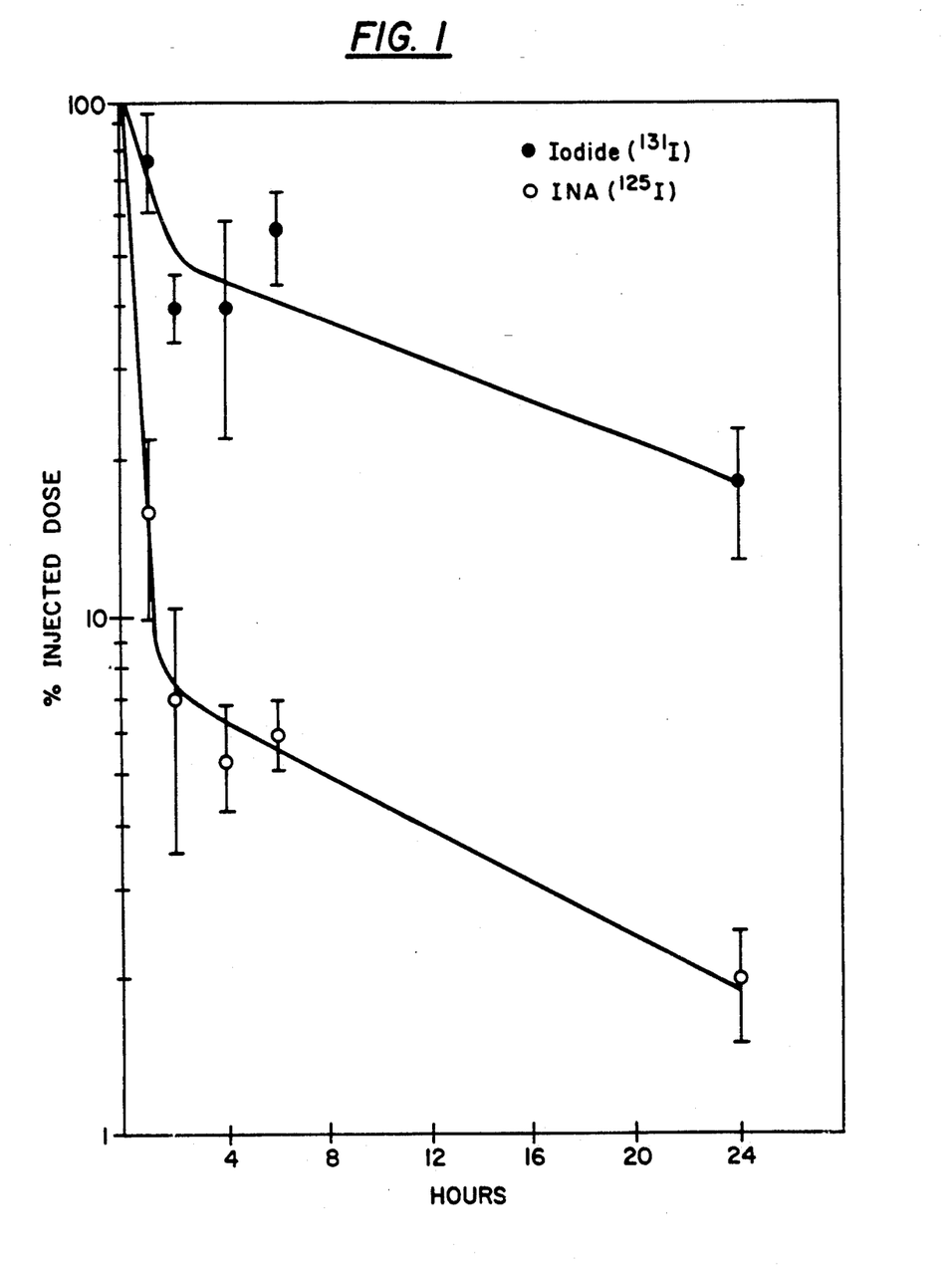
FIG. 1 shows the whole body clearance of 5-[$^{125}$I]iodonicotinic acid (INA) and $^{131}$I.

One approach for decreasing the retention of a nuclide in normal tissues following the administration of labeled antibodies is to couple the isotope in a chemical form which will be excreted rapidly after antibody catabolism. Degradation of antibodies labeled using the SPC method should result in the production of 5-iodonicotinic acid (INA). As shown in FIG. 1, the whole body clearance of INA is considerably faster than iodide.

Figure 2:
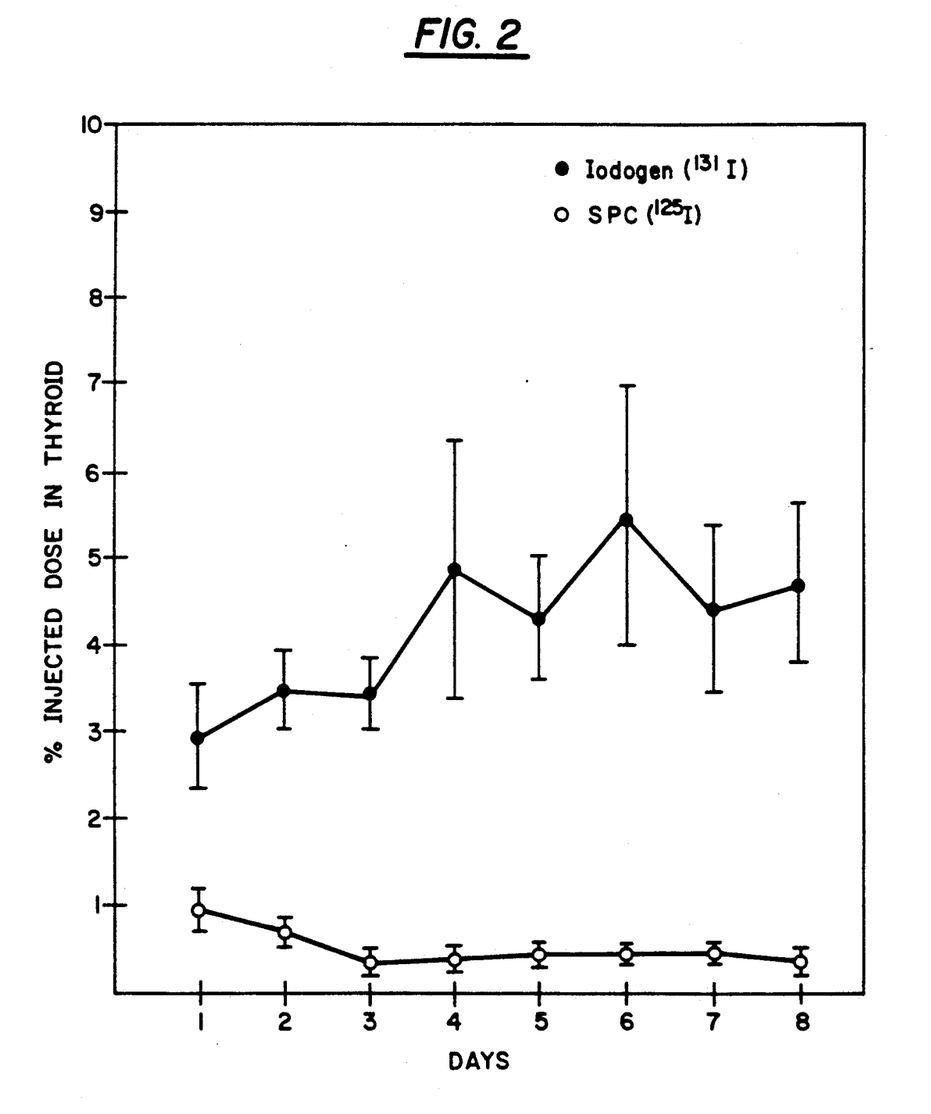
FIG. 2 shows the results of a paired-label study of 110 Ab IgG radioiodinated by iodogen and N-succinimidyl-2,4-dimethoxy-5-(tri-n-butylstannyl)-3-pyridine (SPC) methods.

Several paired-label studies were performed using anti-CEA antibody 110 IgG labeled with either $^{131}$I or 125I using the SPC method. In the first, normal mice were injected with 110 IgG labeled with 125I using the SPC reagent and with 131I using a conventional method, Iodogen. As shown in FIG. 2 and Table 2, use of the SPC method reduced the thyroid uptake of iodine by 250% at day 1. For time points between days 3-8, thyroid uptake was reduced more than 9-fold when 110 IgG was labeled via the SPC reagent.

Figure 3:
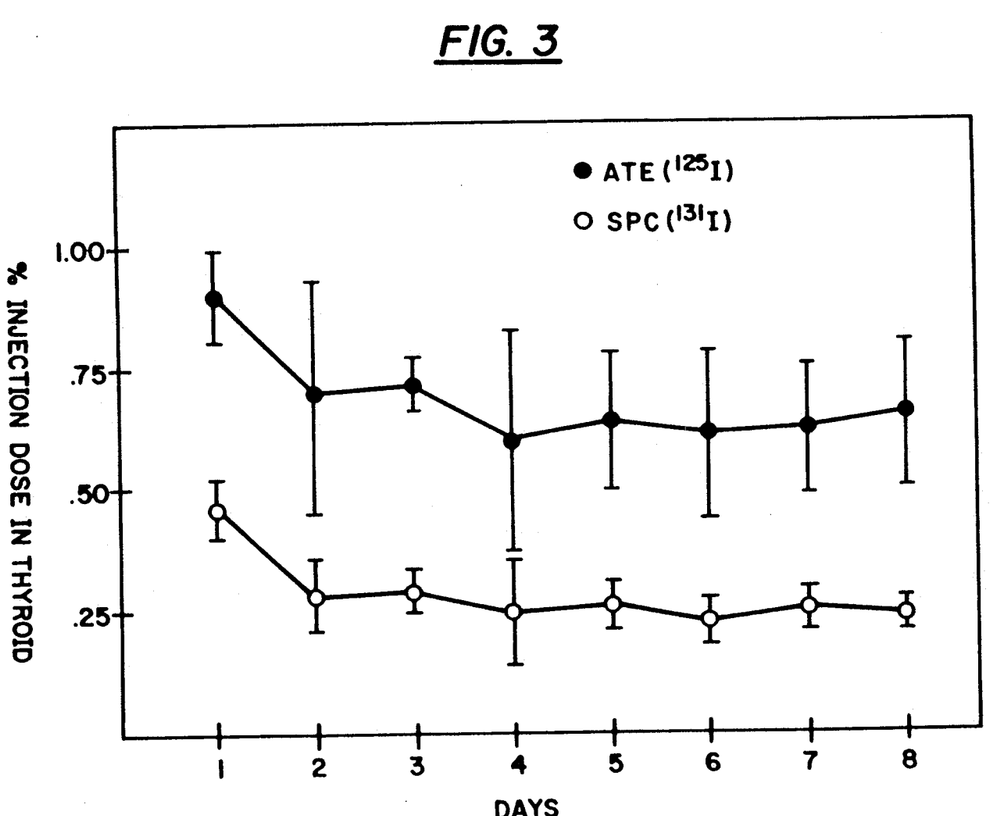
FIG. 3 shows the results of a paired-label study of 110 Ab IgG radioiodinated by the ATE and SPC methods.

In the second experiment, a paired-label study was performed in normal mice injected with 110 IgG labeled with 125I using N-succinimidyl-3-(tri-n-butylstannyl benzoate (ATE—see p. 6, supra) and labeled with 131I using SPC. Table 2 and FIG. 3 show that the SPC method reduced thyroid uptake by a factor of 2 to 3 below that observed with ATE procedure.

Figure 4:
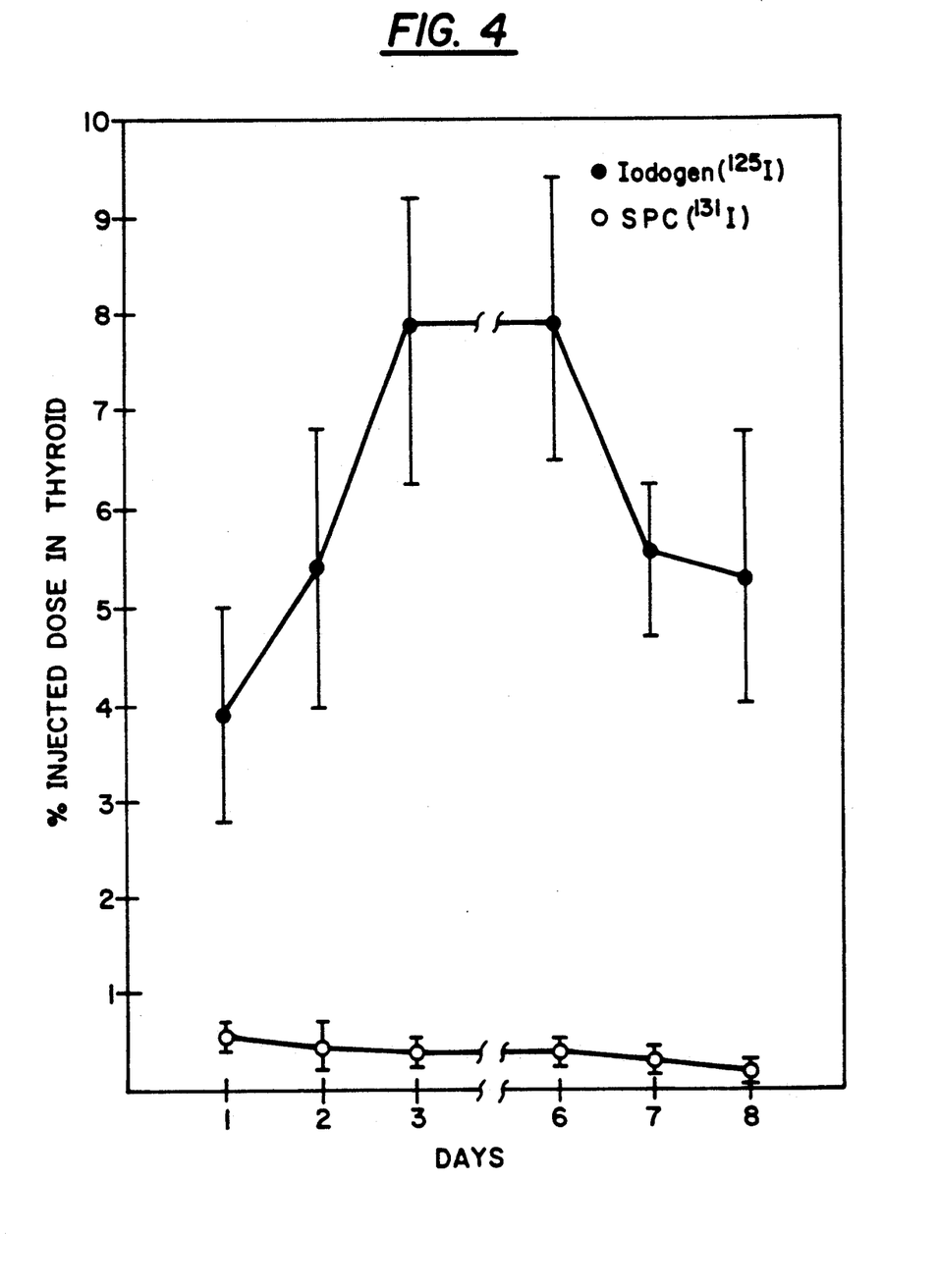
FIG. 4 shows the results of a paired label study of *I-labeled 110 Ab IgG in athymic mice with LS174T xenografts.

The last paired-label experiment was performed in athymic mice bearing human colorectal carcinoma LS174T xenografts. This type of model is extremely important for assessing antibody dehalogenation because of the increased rate of catabolism associated with athymic mice bearing antigen-positive tumors (Pimm and Baldwin, 13 Eur. J. Nucl. Med. 258-263, 1987). As shown in FIG. 4, labeling antibody 110 IgG using SPC reduced thyroid uptake of radioiodine to levels as much as 23 times less than those observed in the same mice with Iodogen.

In conclusion, these results demonstrate that use of the SPC method for radioiodinating antibodies decreases the thyroid uptake of radioiodine when compared to either conventional approached (Iodogen) or this ATE procedure.

TABLE 1

Thyroid and stomach uptake following the injection of 3-[125I]iodonicotinic acid and [131I]iodide in mice

| Time | Thyroid | | Stomach | |
|---|---|---|---|---|
| (hr) | 125I (INA) | 131I (Iodide) | 125I (INA) | 131I (Iodide) |
| 1 | 0.13 ± 0.13 | 7.23 ± 1.27 | 0.69 ± 0.40 | 16.56 ± 8.10 |
| 2 | 0.27 ± 0.09 | 7.23 ± 1.39 | 0.53 ± 0.41 | 12.61 ± 7.33 |
| 4 | 0.44 ± 0.21 | 12.21 ± 3.27 | 0.18 ± 0.03 | 3.53 ± 0.74 |
| 6 | 1.04 ± 0.24 | 23.64 ± 4.95 | 0.24 ± 0.10 | 4.16 ± 1.82 |
| 24 | 0.67 ± 0.19 | 16.95 ± 4.98 | 0.14 ± 0.01 | 0.06 ± 0.02 |

TABLE 2

Summary of thyroid uptake ratios in paired-label studies with 110 anti-CEA antibody radioiodinated using N-succinimidyl-5(tri-n-butylstannyl)-3-pyridine carboxylate (SPC)

| | Normal Mice | | | Athymic Mice |
|---|---|---|---|---|
| Time (days) | Iodogen/SPC | Goat IgG Iodogen/ATC | ATE/SPC | Iodogen/SPC |
| 1 | 2.47 ± 0.52 | 1.7 ± 0.41 | 1.95 ± 0.13 | 7.11 ± 1.67 |
| 2 | 4.70 ± 0.88 | 2.71 ± 0.96 | 2.30 ± 0.22 | 13.46 ± 3.77 |
| 3 | 9.36 ± 3.67 | 3.68 ± 1.21 | 2.49 ± 0.21 | 19.86 ± 3.01 |
| 4 | 12.26 ± 4.94 | 3.65 ± 1.23 | 2.39 ± 0.31 | — |
| 5 | 9.70 ± 1.07 | 9.56 ± 2.73 | 2.42 ± 0.16 | — |
| 6 | 11.15 ± 4.26 | 9.35 ± 2.41 | 2.71 ± 0.41 | 19.57 ± 2.48 |
| 7 | 9.08 ± 2.01 | 8.22 ± 2.51 | 2.41 ± 0.27 | 21.59 ± 7.98 |
| 8 | 11.02 ± 3.40 | 16.26 ± 6.73 | 2.98 ± 0.17 | 23.38 ± 5.11 |

We claim:

1. A method of radiohalogenating macromolecules comprising the steps of:
   (1) radiohalogenating a compound of the formula where L is a linking group selected from the structures with a radioactive halogen selected from the group consisting of F, Cl, Br, I, $^{18}F$, $^{75}Br$, $^{76}Br$, $^{77}Br$, $^{123}I$, $^{125}I$, $^{131}I$, and $^{211}At$ and wherein said radiohalogenation forms a radiohalogenated compound of the formula wherein X is said radioactive halogen and wherein said radiohalogenation is carried out at approximately 80°-85° C.;
   (2) coupling said radiohalogenated compound to a macromolecule.

2. A method according to claim 1 wherein X is $^{125}I$ and L is the group of the formula 3. A method according to claim 1, wherein the macromolecule is selected from monoclonal antibodies and peptides.

* * * * *